United States Patent [19]

Hung et al.

[11] Patent Number: 4,558,010

[45] Date of Patent: Dec. 10, 1985

[54] RECOMBINANT DEOXYRIBONUCLEIC ACID WHICH CODES FOR PLASMINOGEN ACTIVATOR AND METHOD OF MAKING PLASMINOGEN ACTIVATOR PROTEIN THEREFROM

[75] Inventors: Paul P. Hung, Waukegan; Shaw-Guang Lee, Libertyville; Ranajit Roychoudhury, Wadsworth, all of Ill.; Barry J. Ratzkin, Houston, Tex.

[73] Assignee: Abbott Laboratories, North Chicago, Ill.

[21] Appl. No.: 415,491

[22] Filed: Sep. 7, 1982

Related U.S. Application Data

[62] Division of Ser. No. 137,032, Apr. 3, 1980, Pat. No. 4,370,417.

[51] Int. Cl.[4] ............................................. C12P 21/00
[52] U.S. Cl. ..................................... 435/212; 536/28; 536/29
[58] Field of Search ...................... 536/28; 260/112 R; 435/212

[56] References Cited

U.S. PATENT DOCUMENTS

| | | | |
|---|---|---|---|
| 3,355,361 | 11/1967 | Lesuk | 435/215 |
| 3,755,083 | 8/1973 | Novak | 435/215 |
| 3,829,567 | 8/1974 | Butti et al. | 536/28 |
| 3,957,582 | 5/1976 | Stried | 435/215 |
| 4,190,495 | 2/1980 | Curtiss | 435/172 |
| 4,190,649 | 2/1980 | Beljanski | 536/28 |
| 4,237,224 | 12/1980 | Cohen | 435/172 |
| 4,335,239 | 6/1982 | Beljanski | 536/27 |

FOREIGN PATENT DOCUMENTS 2119804A 11/1983 United Kingdom ................ 435/212

OTHER PUBLICATIONS

Chang, et al., Nature, vol. 275, 617–622, (Oct. 1978).

*Primary Examiner*—Ethel G. Love
*Attorney, Agent, or Firm*—James L. Wilcox; Dennis K. Shelton; Martin L. Katz

[57] ABSTRACT

The present invention provides a deoxyribonucleic acid (DNA) segment related to a human plasminogen activator gene. The segment is inserted into a plasmid vector which in turn can be incorporated into a bacterium or other microorganism. The bacterium can then be cultured to produce a plasminogen activator protein having properties of human urokinase.

1 Claim, 2 Drawing Figures

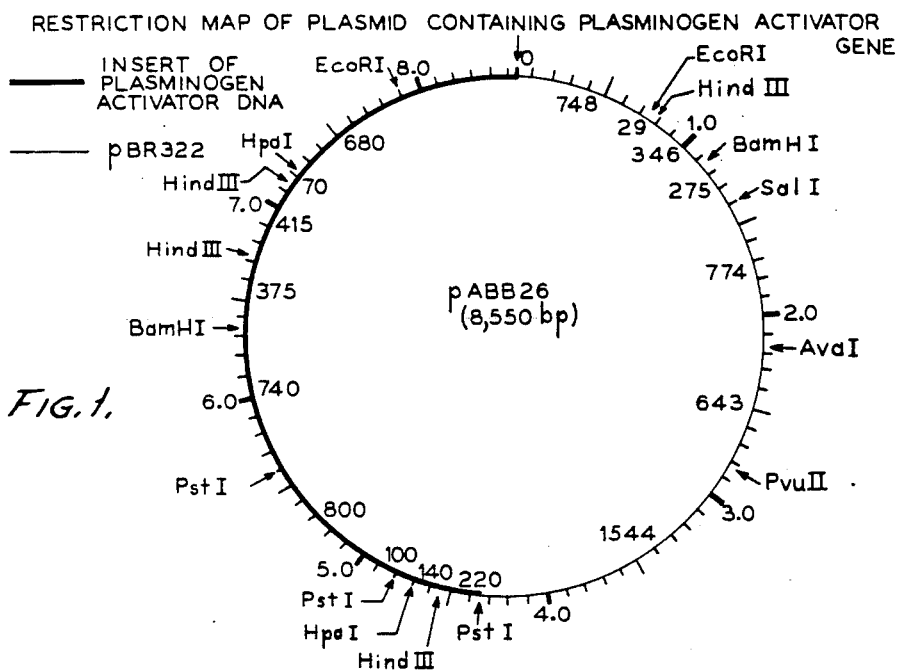
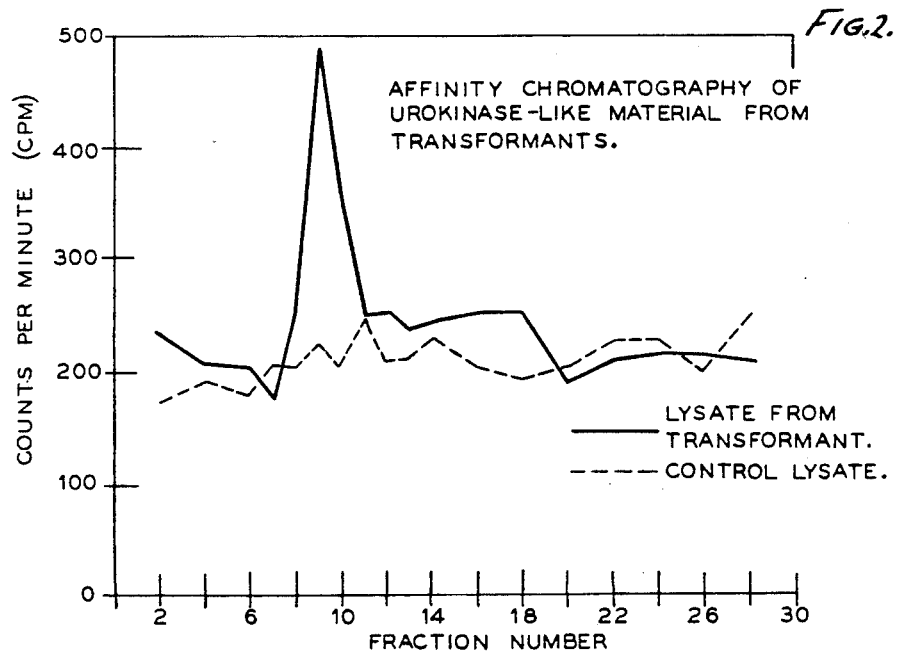

RECOMBINANT DEOXYRIBONUCLEIC ACID WHICH CODES FOR PLASMINOGEN ACTIVATOR AND METHOD OF MAKING PLASMINOGEN ACTIVATOR PROTEIN THEREFROM

This is a division of application Ser. No. 137,032, filed Apr. 3, 1980, now U.S. Pat. No. 4,370,417, issued Jan. 25, 1983.

BACKGROUND OF THE INVENTION

Acute thromboembolic events, venous and arterial thrombosis, pulmonary embolism, intracardiac thrombosis and systemic embolism are difficult to manage. Current medical therapy for the occlusion itself commonly involves anticoagulation. The current medical approach is designed to stop the underlying process and to rely on normal physiologic mechanisms for restoring blood flow and limiting the extent of vascular obstruction or destruction of tissue. Thrombolysis or thrombolytic therapy would be of considerable interest as a means for lysing the offending thromboembolism. By using both anticoagulation and thrombolytic therapy, medical practice would have the means to dissolve thromboemboli quickly and prevent their recurrence. Recently, several approaches to thrombolytic therapy have been under investigation, one being through the systemic infusion of activators of the naturally occurring fibrinolytic enzyme system. One such agent which has undergone extensive study is urokinase. Urokinase is a thrombolytic agent active through the conversion of plasminogen to plasmin. Plasminogen is the naturally occurring plasma precursor which, in the presence of an activator, is converted to plasmin, the proteolytic enzyme capable of hydrolyzing fibrin. Urokinase is a complex protein of unknown structure which is found in human urine in trace amounts. It is a potent blood clot lysing agent and when injected in amounts far greater than those which exist naturally in the blood will promote the dissolution of blood clots. It was first described in 1951 after which processes for the isolation and purification of uorkinase from human urine were developed. Methods for the isolation and purification of urokinase are described in many publications, such as U.S. Pat. Nos. 2,983,647; 3,256,158; 3,477,910 to 3,477,913 and 3,544,427. However, the logistics of urine collection and processing makes this source of urokinase impractical, four million CTA (Committee on Thrombolytic Agents) units of urokinase requiring the processing of about 1,500 liters of urine. Fibrinolytic activity in cultures of human kidney cells was later demonstrated, and it was found that this activity was immunologically indistinguishable from urinary urokinase. Even using tissue culture processes, high production costs result, and, consequently, other methods for the preparation of urokinase are desirable.

SUMMARY OF THE INVENTION

The present invention provides a modified plasmid with inserted deoxyribonucleic acid (DNA) which codes for plasminogen activator related to human urokinase. The modified plasmid can be introduced into a bacterium or other microorganism which can then be cultured to produce urokinase-like material in the same manner as the manufacture of antibiotic compounds. The modified plasmid was obtained by direct manipulation of nucleotide sequences in the plasmid. For purposes of description, the invention will be described with reference to the bacterium E. coli K-12 Strain X1776 as described in "Recombinant Molecules, Impact on Science and Society," Beers, R. F. and Bassett, E. G., editors, Raven Press, New York, page 45, 1977, and the plasmid or vector therefrom, pBR322, as described by Bolivar, et al. (Gene: 2, page 95, 1977). Applicants have inserted into a bacterium a DNA segment which codes for a human plasminogen activator, urokinase. The microorganism thus obtained acquires the new capability of producing plasminogen activators which possess immunological and plasminogen activator properties similar to those of urokinase isolated from tissue culture of human embryonic kidney cells. The method for this genetic engineering comprises, briefly: (1) isolation of messenger ribonucleic acid (mRNA) from human embryonic kidney cells; (2) demonstration of the presence of urokinase mRNA in the isolated mRNA; (3) laboratory synthesis of complementary DNA (cDNA) from mRNA suitable for recombinant DNA synthesis; (4) synthesis of recombinant DNA containing the DNA synthesized in (3) and a vector or plasmid DNA; (5) transformation of the bacterium with the recombinant DNA and detection and selection of transformants for plasminogen activator production; and (6) isolation of plasminogen activators from the transformants and characterization of chemical and biological properties.

The new technique of manipulation of nucleotide sequences permits deliberate introduction of known or identified nucleotide sequences from one strain or species into another thereby conferring a desired property. With reference to the double helix structure of DNA, both of the interwound and complementary strands of the DNA molecule are made up of four deoxyribonucleotides: deoxyriboadenosine-5'-phosphate (dAMP), thymidine-5'-phosphate (TMP), deoxy-riboguanosine-5'-phosphate (dGMP) and deoxyribocytidine-5'-phosphate (dCMP), which are linked through the phosphate groups. The genetic message of each strand is embodied in the particular sequence of deoxyribonucleotides. The sequence of nucleotides in a given DNA molecule determines the sequence of amino acids in a particular protein and the sequence of amino acids in turn specifically establish both the structure and function of the protein. Hence, the nucleotide sequence of DNA precisely specifies the protein building properties of the organism.

The recombinant DNA procedure begins with cleavage of the strands of DNA by proteins known as restriction endonuclease enzymes which are isolated from bacteria. The enzymes break the chain of DNA at particular sequences. The break does not always occur at the same point on two strands so that separate strands may have complementary ends and hence under suitable conditions will bind together so that they can be coupled end to end. If the same restriction enzyme is used on the DNA from two different sources, both of which have the appropriate target sequence, then sequences with ends which will bind will result. Hence, two sequences from any source can be recombined into a single DNA molecule. Another way of obtaining DNA for insertion is to reverse transcribe messenger RNA into double stranded complementary DNA. The synthesized DNA then can be inserted into a plasmid as described, hereinafter. This method of obtaining DNA is preferred since genes of mammalian chromosomal DNA often contain sequences not coding for protein, thus interupting the colineality of genetic information transfer from DNA to protein. In bacterium such as *Escherichia coli*, in addition to its single circular chromosome it may have one or more independently replicating smaller circles of DNA known as plasmids or extrachromosomal elements which are hereditary units physically separate from the chromosome of the cell. These plasmids or vectors can be isolated from the bacteria, opened or cleaved by restriction enzymes, and used as one component of a recombinant. After connecting the plasmid DNA with the DNA to be inserted, the circular form of the plasmid can be closed, and the plasmid returned to the cell. There it will resume replication, duplicating not only its own natural nucleotide sequence but also the one which has been added. A strain of bacteria is, therefore, obtained which will maintain copies of the inserted nucleotide sequence as the bacterium propagates.

DRAWINGS

The invention will be better understood with reference to the following drawings in which:

FIG. 1 is a schematic illustration of a restriction map of a plasmid-containing DNA which codes for plasminogen activator protein related to urokinase.

FIG. 2 is a chart illustrating data obtained from affinity chromatography of urokinase-like material from transformants.

DETAILED DESCRIPTION

Plasmids are believed to consist of doublestranded DNA molecules and to include at least one replication site. Referring to FIG. 1 of the drawings, there is illustrated schematically the *E. coli* plasmid pBR322 into which has been inserted a DNA segment coding for plasminogen activator related to urokinase. The plasmid or vector pBR322 is described by Bolivar, et al. (Gene, 2, page 95, 1977). As illustrated in FIG. 1, the pBR322 plasmid is broken open by a restriction enzyme, at a position hereinafter described, as the Pst I site, and the DNA segment which codes for plasminogen activator is inserted therein. Binding occurs because a sequence on one strand lies immediately opposite a complementary sequence, complementarity depending on the chemical affinity between the nucleotides cytosine and guanine or adenine and thymine, respectively. The sum of these bonds repeated along the length of the strands holds the strands together. An alternative way to connect two DNA fragments is by blunt end ligation using ligase. The numerical values referred to in FIG. 1 represent the numbers of base pairs between the sites indicated and are approximate in nature. As an example, the number of inserted base pairs between the original Pst I sites of the pBR322 plasmid is approximately 4,200. The positions or sites along the diameter in FIG. 1 represent positions at which specific sequences of nucleotides occur and which can be cleaved by specific restriction endonuclease enzymes. The code in FIG. 1 indicates the approximate position of each site and the particular restriction enzyme which will cut the DNA strand at that particular sequence of nucleotides.

FIG. 1 represents one embodiment of the invention and as exemplified is an *E. coli* plasmid with inserted DNA which codes for urokinase-like material. The recombinant DNA, namely the restructured plasmid containing DNA which codes for urokinase-like material, is returned into a suitable host organism which as exemplified is *E. coli* K12 strain X1776. There it can resume replication duplicating not only its own native sequence but also the sequence which has been inserted.

Other suitable organisms can be selected from the genus Escherichia, Saccharomyces, Bacillus, Neurospora, or Streptomyces, among others. Examples of suitable species of microorganisms are *Escherichia coli, Saccharomyces cerevisiae, Bacillus subtilis,* and *Neurospora crassa.*

The present invention in particular provides a bacterium from the genus, Escherichia, containing therein a stable plasmid which produces plasminogen activator protein related to urokinase in immunogenic and biological properties. Cultures of *E. coli* X1776 p ABB26 have been deposited with the ARS Culture Collection, U.S. Department of Agriculture, Peoria, Ill. which deposit has been accorded Accession No. B12122.

EXAMPLE I

Isolation of mRNA from Human Embryonic Kidney Cells

Total mRNA from urokinase-producing cells was isolated as follows: Human embryo kidney (HEK) cells were grown in tissue culture to confluency in 7–10 days in Eagle's medium (E199) with 10 percent fetal calf serum. The cells were maintained in a protein hydrolysate medium without serum for an additional 7 days before harvest. HEK cells were scraped off the roller bottles, washed in saline containing heparin (10 units/ml) and total RNA was isolated by the guanidine thiocyanate method of Ullrich et al. (Science, 196, 1313, 1977) with the exception that the extraction with guanidine salt was done at pH 7.0 in phosphate buffered saline (PBS) buffer. The RNA was precipitated with ethanol and dissolved in 33 mM N-2-hdroxyethyl piperazine-N'-2-ethane sulfonic acid (HEPES) buffer, pH 7.0. Polyadenylic acid (Poly A) containing mRNA was isolated from the total RNA by affinity chromatography on polyuridylic acid (Poly U) Sephadex G-10 column as described by Deeley et al. (J. Biol. Chem. 252, 8310, 1977). The column material was synthesized according to the method of Coffin et al. (J. Mol. Biol. 86, 373, 1974). The RNA was passed twice in the column to yield total mRNA (1.1 mg from 39 mg total RNA). The urokinase mRNA was further enriched and isolated from the total mRNA by sucrose density gradient centrifugation. The total RNA was dissolved in TES-2 buffer (10 mM Tris-HCl, pH 7.4; 20 mM NaCl; 0.5 mM EDTA; 0.4 percent sodium dodecylsulfate (SDS) in a concentration of about 10 $A_{260}$ per ml. The RNA was heated at 65° C. for 15 min., applied to a linear (10–30 percent) sucrose gradient and centrifuged in a SW 27 rotor at 20° C. for 12 hr. at 25,000 rpm in a Beckman L5-65 ultracentrifuge. The gradient was then fractionated into fractions (0.5 ml/fraction) and the $A_{260}$ reading determined. The RNA greater than 28S was pooled and ethanol precipitated, washed with 33 mM NaCl in 70 percent ethanol and then with 95 percent ethanol. It was dried and dissolved in 33 mM HEPES buffer, pH 7.0. From 1 mg of RNA applied to the gradient, 73 ug of the RNA greater than 28S were obtained. The RNA was used to demonstrate the presence of urokinase mRNA in cell-free protein synthesis and for cDNA synthesis.

EXAMPLE II

Demonstration of the Presence of Urokinase mRNA in the Isolated RNA Preparations by Cell-free Protein Synthesis The cell-free protein synthesizing system from rabbit reticulocytes was nuclease treated to deplete endogenous mRNA according to the method of Pelhem and Jackson (*Eur. J. Biochem.*, 67, 247, 1976). Cell-free protein synthesis and immunoprecipitation were carried out according to the method of Rhodes et al. (*J. Biol. Chem.*, 248, 2031, 1973). Incubations were performed in a final volume of 45 ul containing 20 percent (vol/vol) reticulocyte lysate, 2 mM adenosine triphosphate (ATP), 0.2 mM guanidine triphosphate (GTP), 10 mM creatine phosphate, 2 ug creatine kinase, 3 mM dithiothreitol, 75 mM KCl, 3 mM $MgCl_2$, 30 mM HEPES, pH 7.6, 20 uM of amino acid mixtures without methionine, 5 uCi $^{35}$S-methionine and 1 ug of purified messenger RNA. The mixtures were incubated at 25° C. for 1 hr. and then stopped by chilling and adding 25 ul of 0.1 M methionine, 10 percent Triton X-100 and 10 percent sodium deoxycholate. Trichloroacetic acid insoluble counts for the total incorporation were obtained by pipetting 5 ul aliquots onto 3 MM filter paper discs, which were washed in 7.5 percent trichloracetic acid (TCA) containing 0.2 percent D,L-methionine. The paper discs were then heated at 90° C. for 15 min. in the same TCA-methionine solution and dried before counting in a scintillation counter.

Immunoprecipitation of synthesized $^{35}$S-peptides was performed as described by Rhodes, et al. (see above), with the modification that each antigen-antibody precipitate was sedimented through a sucrose cushion consisting of 200 ul of 0.5 M sucrose, 1 percent Triton X-100, 1 percent sodium deoxycholate, and 0.2 M DL-methionine. Purified urokinase (0.5 ug) was added to the reaction mixture as carrier, and immunoprecipitation was done by adding 5-10 ug of rabbit antiurokinase (IgG fraction). The second antibody (goat antirabbit IgG, 100-200 ug) was added and the reaction mixture incubated further at 4° C. for 18 hrs. The final precipitates were washed and resuspended in 10 M urea, 5 percent SDS and 5 percent mercaptoethanol and heated at 60° C. for 30 min. Aliquots were counted in a scintillation counter for $^{35}$S incorporation. The content for the urokinase specific mRNA was expressed as the percentage of immunoprecipable counts over the total counts precipitated by TCA. In this reaction condition, $1 \times 10^5$ cpm per ul of the reaction mixture could be TCA precipitated when 1 ug of purified rabbit globin messenger RNA is used in the reaction mixture. Less than 1 percent of the radioactivity was immunoprecipitated by urokinase antibody in the rabbit globin mRNA control. However, Poly A containing mRNA from human embroyonic kidney (HEK) cells gave 10 percent of the TCA insoluble radioactivity as immunoprecipable counts. Messenger RNA greater than 28S by sucrose density gradient centrifugation showed that 40-60 percent of the TCA precipitable radioactivity was immunoprecipated by urokinase antibody.

Cell-free protein synthesis dependent on added mRNA was also carried out in the wheat-germ system as described by Roberts and Peterson (*PNAS*, 70, 2330, 1973). Immunoprecipitation was carried out as described above in the rabbit reticulocyte system. Messenger RNA greater than 28S from sucrose density gradients gave as much as 90 percent of the TCA insoluble counts as the immunoprecipable counts.

EXAMPLE III

Complementary DNA (cDNA) Synthesis from mRNA

Single stranded cDNA was synthesized by reverse transcription of mRNA according to the method of Friedman and Rosbash (*Nucleic Acids Res.*, 4, 3455, 1977) with the following modifications. The reaction mixture (500 ul) for annealing oligo dT primer with mRNA contained 20 mM Tris-HCl, pH 8.5, 20 mM KCl, 4mM $MgCl_2$, 20 ug of poly A containing mRNA and 1.5 ug of $dT_{30}$. The final reaction mixture (1 ml) for cDNA synthesis contained 50 mM TrisHCl, pH 8.5, 50 mM KCl, 10 mM $MgCl_2$, 10 mM dithiothreitol (DTT), 100 ug actinomycin D, 1 mM each of deoxyadenosine triphosphate (dATP), deoxyguanidine triphosphate (dGTP), thymidine triphosphate (TTP), 800 uM [$\alpha$-$^{32}$P] dCTP and 325 units of AMV reverse transcription. After 30 min. of incubation at 42° C., another 325 units of the enzyme were added. After 2 hr. of incubation, the reaction was terminated by adding 50 ul of 0.5 M ethylenediamine tetraacetic acid (EDTA). To the solution was added 40 ul of 10 M NaOH followed by incubation at room temperature for 18-20 hours. The solution was then neutralized to pH 8.5 by adding HEPES powder with slow stirring. The solution was then subjected to phenol extraction, Sephacryl S-300 gel filtration and ethanol precipitation of the excluded fractions which contained the high molecular weight cDNA. The yield was 15-25 percent. The CDNA product was subjected to electrophoresis in 3.5% polyacrylamide slab gel (20×40×0.3 cm) in 7M urea. A Hind III endonuclease digest of lambda DNA was used as length markers. After autoradiography of the gel, the single-stranded cDNA with predominant species of 3000-6000 nucleotide residues was detected.

The second strand of the cDNA was synthesized by using the large fragment of DNA polymerase I from *E. coli* similar to the reaction condition described by Jacobsen, et al., (*Eur. J. Biochem.*, 45, 623, 1974). The reaction included 24 units of DNA polymerase I (the large fragment) 1.4 nmoles of cDNA, 0.1 M HEPES, pH 7.0, 400 uM each of dATP, deoxycytosine triphosphate (dCTP), dGTP, and TTP, 10 mM $MgCl_2$, 10 mM dithiothreitol and 70 mM KCl in a 200 ul reaction volume. Incubation was done at 15° C. for 1.5 hours. Then 20 ul of 0.5 M EDTA were added and DNA was purified by phenol extraction and ethanol precipitation.

The double stranded cDNA mentioned above was then treated with $S_1$ nuclease (1250 units) for three hours at 15° C. in the presence of 30 mM sodium acetate pH 4.6, 1 mM $ZnSO_4$, 250 mM NaCl and 100 ug/ml of *E. coli* tRNA. About 58 percent (approximately 0.5 ug) of the DNA was recovered after the treatment. Then the DNA was centrifuged in a linear sucrose density gradient (15-30 percent in saline-tris-EDTA (STE) buffer, 10 mM NaCl, 10 mM Tris pH 8.0, 1 mM EDTA) in a swing bucket SW 40 rotor at 22° C. for 16 hrs. at 40,000 rpm in a Beckman L5-75 ultracentrifuge. DNA greater than 2000 base pairs was pooled, ethanol precipitated and used to tail with poly C tracts for recombinant DNA synthesis.

EXAMPLE IV

Synthesis of Recombinant DNA

Addition of homopolymer tracts to the double-stranded cDNA was carried out without the use of exonuclease as described by Roychoudhury, et al., (*Nucleic Acid Res.*, 3, 863, 1976). The reaction mixture (300 ul) contained 100 mM potassium cacodylate pH 6.9, 30 mM Tris base, 1 mM $CoCl_2$, 200 uM DTT, 6 nmoles of duplex cDNA in total nucleotide residues, 100 uM $[\alpha-{}^{32}p]dCTP$ and 240 units of terminal transferase. The reaction was terminated after 20 minutes by addition of 30 ul of 0.5 M EDTA and 300 ul of neutralized phenol. After thorough mixing, the contents were centrifuged at 1500 xg for 10 min. and the aqueous layer was withdrawn. The phenol layer was extracted twice with 100 ul of 100 mM NaCl, pH 8.0 and the combined aqueous layer was ether extracted and ethanol precipitated.

From approximately 20 pmoles in 3'—OH ends in the double stranded cDNA, 1400 pmoles of [32p] dCMP were incorporated. This accounted for an addition of 70 dCMP residues added per DNA strand. The linear plasmid DNA was obtained as follows: The reaction mixture (100 ul) contained 10 mM Tris-HCl, pH 7.8, 10 mM $MgCl_2$, 10 mM DTT, 50 mM NaCl, 10 ug of pBR322 DNA and 5 units of Pst I. After 20 hrs. at 37° C., an aliquot (5 ul) of the reaction mixture was analyzed by agarose gel electrophoresis to check for completeness of digestion. The linear DNA was then phenol extracted and isolated by ethanol precipitation.

The DNA was suspended in 100 ul of 10 mM Tris-HCl, pH 8.0, 0.5 mM EDTA and incubated in terminal transferase buffer as described above containing 100 uM $[^3H]$ dTTP and 240 units of terminal transferase. At intervals of 0, 1, 2, 3, 4 and 5 min. at 42° C., aliquots (5 ul) were monitored for acid insoluble radioactivity. The remaining solution after 5 min. of incubation was phenol extracted and ethanol precipitated. During this period a total of 130 pmoles of dGMP residues were incorporated. To the DNA sample containing 5.4 pmoles of 3'—OH ends, an average of 24 residues were added per strand of pBR322 DNA.

The large double-stranded cDNA tailed with polydeoxycitydilic acid (poly dC) (about 0.15 pmole) was annealed to an equivalent amount of the polydeoxyguanilydic acid (poly dG) tailed pBR322 DNA in 0.1 M NaCl in a 100 ul volume. The mixture was heated to 65° C. for 3 min. and left at 42° C. for 16 hours to anneal the DNA preparations.

EXAMPLE V

Transformation of *E. coli*

The procedure of Curtiss et al. (Procedure described in "Genetic Engineering", CRC Press, 1978, Editor, Charkrabarty, A. M., Chapter 3, by W. Salser, p. 73) was used to transform X1776 (F- ton A53 dapD8 minA1 minB2 supE42 qalΔ40⁻ rfb-2 nalA25 oms-2 thyA57 metC65 oms-1 [bioH-asd] Δ29 cycB2 cycA1 hsdR2) with the annealed DNA mixture. Cells were grown to 0.3 $A_{600}$ at 37° C. in supplemented L broth (diaminopimelic acid 100 ug/ml, nalidixic acid 25 ug/ml and thymine 40 ug/ml) and were centrifuged at 1700 xg for 10 minutes at room temperature to collect the pellet. The cells were suspended in 10 mM NaCl (½ volume), centrifuged and suspended again in ½ volume Ca buffer (75 mM $CaCl_2$, 140 mM NaCl, 10 mM Tris HCl, pH 7.0). After 30 minutes at room temperature, the cells were centrifuged and resuspended in 1/10 volume of Ca buffer and chilled to 0° C. Two volumes of cells were mixed with one volume of DNA, held at 0° C. for 30 minutes, heated at 42° C. for 1 minute and let rest at room temperature for 10 minutes, mixed with 10 volumes supplemented L-broth and incubated at 37° C. for 100 minutes. The cells were plated onto supplemented L-agar containing 12.5 ug tetracycline by pipetting portions of the culture into 2 ml soft L-agar (0.6 percent) and overlaying onto plates. The plates were incubated two days at 37° C.

A total of 32 tetracycline-resistant transformants were obtained. Of these, four were ampicillin-sensitive ($AMP^s$) and had inserts in their plasmids. Three had similar inserts of approximately 4.2 kilo base pairs. A restriction map of one of these plasmids is shown in FIG. 1.

EXAMPLE VI

Detection, Isolation and Characterization of Plasminogen Activator Protein Products in Transformants Ampicillin-sensitive, tetracycline-resistant *E. coli* transformants containing recombinant DNA were screened for possible expression of urokinase-like materials using immunological detection methods. The solid phase radioimmunoassay (RIA) using plastic microtiter plates was done according to the method of Hitzeman, et al. (Methods in Enzymology: Recombinant DNA, 1979) with a slight modification. In the direct RIA method using cyanogen bromide activated paper, urokinase or urokinase-like material was reacted directly with cyanogen bromide activated paper discs, and then detected by binding of $^{125}I$-labeled antiurokinase antibody.

The cell lysate was prepared according to Seeburg et al. (Nature, 276 795, 1978). Five hundred ml of *E. coli* transformants were grown overnight and the cells collected by centrifugation at 10,000 xg for 10 min. The cells were washed with 10 mM Tris (pH 8.0) and 1 mM EDTA and resuspended in 5.0 ml of the same buffer. After addition of 0.5 ml of lysozyme (5 mg/ml), the mixture was kept on ice for 30 minutes. $MgCl_{12}$ was added to a final concentration of 10 mM with 0.1 ml each of DNase (1 mg/ml), RNase (5 mg/ml) and NP-40 (5%). Incubation proceeded for 1 hr. at 4° C. and the mixture was cleared by centrifugation (10,000 xg, 20 min., 0° C.). The supernatant was used for the screening of urokinase-like material.

a. Aliquots of the lysate were spotted on cyanogen bromide paper (the direct RIA method) and reacted with $^{125}I$-urokinase antibody as described previously by Hitzeman et al. (See above.) Known amounts of urokinase were also spotted as the positive control. One transform ant harboring recombinant DNA, pABB26, showed strong positive reaction.

b. Aliquots of the lysate were diluted 10 times with a buffer (0.1 M potassium phosphate, pH 7.0, and 0.4 M NaCl) and loaded on 1×5 ml benzamidine affinity column (Holmberg, et al., BBA 445, 215, 1976). The column was washed thoroughly with the buffer until $A_{280}$ readings reached background. The column was eluted with the elution buffer (0.1 M sodium acetate, pH 4.0, and 0.4 M NaCl) to collect fractions. Aliquots from each fraction were assayed by the solid phase RIA.

When the cell lysate from Transformant X1776 (pABB26) was passed through the benazmidine affinity column, some $A_{280}$ material from the lysate was retained in the column and eluted only by low pH and high salt. These retained materials showed positive reaction in the solid phase RIA for urokinase, whereas the control lysate from Transformant X1776 (pBR322) was negative (FIG. 2). The products were further characterized for their molecular sizes by SDS polyacrylamide gel electrophoresis, followed by filteraffinity transfer (J. Biol. Chem. 254, 12240, 1979) onto cyanogen bromide activated paper. $^{125}$I-labelled urokinase-specific antibody revealed five discrete sizes of plasminogen activator protein with approximate molecular weights of 32,000, 52,000, 87,000, 124,000 and 154,000.

Plasminogen activator activity was measured using a sensitive $^{125}$I fibrinolysis assay modified from Unkeless et al. (*J. Exp. Med.*, 137, 85–111, 1973). Rigid microtiter plates were coated with $^{125}$I fibrinogen (2 ug, $10^5$ cpm per well) and the fibrinogen converted to fibrin clots using plasminogen-free thrombin (0.1 units/well). Assays were conducted in a total volume of 70 ul containing 0.1 M Tris HCl, pH 8.1, 0.025 percent human serum albumin and 2.5 ug/ml plasmin-free plasminogen prepared by affinity chromatography on lysine Sepharose. The range of the assay was from 0.05 Ploug units/ml to 10 units/ml and could detect as little as 0.002 units. Since crude lysates of *E. coli* were inhibitory in this assay, transformant preparations were partially purified by ion exchange chromatography or affinity chromatography on benzamidine-Sepharose prior to assay (Table 1).

When urokinase affinity column eluates of Transtormant X1776 (pABB26) were tested using this assay, significant fibrinolytic activity was detected whereas samples from X1776 transformed with pBR322 showed no such activity. Furthermore, immune precipitation with antisera specific for human urokinase was capable of removing this activity from solution providing confirmation of the immunochemical relatedness of plasminogen activator activity from Transformant X1776 (pABB26) and human urokinase (see Table 1).

TABLE 1

Plasminogen Activator Activity in Bacterial Transformants[a]

| Sample | Antisera[b] | CPM | Milli-Units | % Activity Remaining |
|---|---|---|---|---|
| Background | — | 798 | — | — |
| X1776 (pBR322) | — | 952 | — | — |
| X1776 (pABB26) | — | 10887 | 50 | 100 |
| " | Anti-UK | 1479 | 2.3 | 4.6 |
| " | NRS | 5127 | 23 | 46 |
| Urokinase Std. | — | 7564 | 35 | 100 |
| " | Anti-UK | 1630 | 2.5 | 7 |
| " | NRS[c] | 3458 | 12 | 35 |

[a] Plasminogen activator activity was measured as described in the text.
[b] 10 ul of a 1:10 dilution of the indicated rabbit antiserum in PBS were added to 25 ul of sample solution for 60 min. on ice. The immune complexes were cleared from solution using 25 ul of a 10 percent (V/V) suspension of glutaraldehyde fixed *S. aureus* according to Kessler (J. Immunology, 115, 1617, 1975). 35 ul of the resulting supernatant were assayed.
[c] NRS - normal rabbit serum

EXAMPLE VII

Growth of *E. coli* Strain X1776 (pABB26)

Cells of *E. coli* Transformants X1776 (pABB26) were grown in L-broth (J.H. Miller *Experiments in Molecular Genetics* Cold Spring Harbor Laboratory, 1972) containing 12.5 ug/ml tetracycline hydrochloride. In addition, M9 medium (J.H. Miller *Experiments in Molecular Genetics* Cold Spring Harbor Laboratory, 1972) which contained 0.5% casamino acids, 0.5% D-glucose, 0.5 ug D-biotin, 100 ug L-diaminbpimelic acid, 40 ug nalidixic acid and 12.5 ug tetracycline hydrochloride all per ml. was also used for growth and production of plasminogen activators from the above strains. Cells were grown at 37° C. with shaking and were generally harvested for the purpose of detecting plasminogen activator production after full growth had been attained.

What is claimed is:

1. The plasminogen activator protein produced by a polydeoxribonucleotide segment which codes for plasminogen activator protein included in a transformant microorganism, said product having substantially the characteristics of urokinase.

* * * * *

UNITED STATES PATENT AND TRADEMARK OFFICE
CERTIFICATE OF CORRECTION

PATENT NO. : 4,558,010
DATED : December 10, 1985
INVENTOR(S) : Paul P. Hung, et al.

It is certified that error appears in the above—identified patent and that said Letters Patent is hereby corrected as shown below:

On page 1, the title page, at "Inventors:", please delete "Paul P. Hung, Waukegan; Shaw-Guang Lee, Libertyville; Ranajit Roychoudhury, Wadsworth, all of Ill.; Barry J. Ratzkin, Houston, Tex." and insert "Paul P. Hung, Waukegan; Shaw-Guang Lee, Libertyville; Ranajit Roychoudhury, Wadsworth, all of Ill.; Barry J. Ratzkin, Houston, Tex.; W. Jürgen Schrenk, Weilheim, Fed. Rep. of Germany; Michael C. Chen, Painted Post, N.Y."

Signed and Sealed this

Fifth Day of August 1986

[SEAL]

Attest:

DONALD J. QUIGG

Attesting Officer  Commissioner of Patents and Trademarks